United States Patent
Aue et al.

(10) Patent No.: US 7,488,318 B2
(45) Date of Patent: Feb. 10, 2009

(54) UROLOGICAL RESECTOSCOPE HAVING A NON-ROTATING INSTRUMENT SUPPORT

(75) Inventors: Thomas Aue, Hamburg (DE); Werner Buβ, Reinbek (DE); Pieter Brommersma, Bargteheide (DE); Felix Nuβbaum, Hamburg (DE)

(73) Assignee: Olympus Winter & IBE GmbH, Hamburg (DE)

( * ) Notice: Subject to any disclaimer, the term of this patent is extended or adjusted under 35 U.S.C. 154(b) by 639 days.

(21) Appl. No.: 10/531,837

(22) PCT Filed: Oct. 2, 2003

(86) PCT No.: PCT/EP03/10952

§ 371 (c)(1),
(2), (4) Date: Apr. 18, 2005

(87) PCT Pub. No.: WO2004/037101

PCT Pub. Date: May 6, 2004

(65) Prior Publication Data

US 2006/0009761 A1  Jan. 12, 2006

(30) Foreign Application Priority Data

Oct. 19, 2002 (DE) ................................ 102 48 839

(51) Int. Cl.
*A61B 18/18* (2006.01)
*A61B 1/00* (2006.01)
(52) U.S. Cl. ........................................ 606/46; 600/105
(58) Field of Classification Search ............. 606/46–50; 600/104–105
See application file for complete search history.

(56) References Cited

U.S. PATENT DOCUMENTS

| 2,008,525 | A |   | 7/1935 | Wappler |
| 3,752,159 | A | * | 8/1973 | Wappler ...................... 606/46 |
| 3,835,842 | A | * | 9/1974 | Iglesias ...................... 600/105 |
| 4,149,538 | A |   | 4/1979 | Mrava et al. |
| 4,423,727 | A | * | 1/1984 | Widran et al. ................. 606/46 |
| 4,430,996 | A | * | 2/1984 | Bonnet ........................ 606/46 |
| 4,726,370 | A |   | 2/1988 | Karasawa et al. |
| 5,112,330 | A |   | 5/1992 | Nishigaki et al. |
| 5,133,713 | A | * | 7/1992 | Huang et al. ................... 606/46 |
| 5,423,813 | A |   | 6/1995 | Kaiser et al. |
| 5,658,280 | A | * | 8/1997 | Issa ............................. 606/46 |
| 6,699,185 | B2 | * | 3/2004 | Gminder et al. ............. 600/157 |

\* cited by examiner

*Primary Examiner*—Michael Peffley
(74) *Attorney, Agent, or Firm*—Rankin, Hill & Clark LLP

(57) ABSTRACT

A urological resectoscope having a tubular shaft (3) is disclosed, having a fixed optical guide tube (2), within which there is an optical system (1) that projects distally beyond the optical guide tube. An elongate, rod-shaped carrier (4) is provided, which carries a cutting instrument (6) at its distal end. The carrier (4) is longitudinally moveably mounted in the tubular shaft (3) outside the optical guide tube (2). The carrier is held distally from the optical guide tube (2) with a sliding tube (8) on the optical system (1) at a radial spacing from the axis of the optical system (1). The carrier is also secured in the peripheral rotary direction to the optical guide tube (2) with a rotary lock (9, 10). The rotary lock has a bar (9) parallel to the carrier (4) and connected to it and a distally open elongate slot (10) in the optical guide tube (2).

3 Claims, 1 Drawing Sheet

UROLOGICAL RESECTOSCOPE HAVING A NON-ROTATING INSTRUMENT SUPPORT

BACKGROUND OF THE INVENTION

1. Field of the Invention

The invention relates to a urological resectoscope with a tubular shaft having a fixed optical guide tube, within which there is an optical system.

2. Description of Related Art

Urological resectoscopes, as are disclosed in DE 3603758 A1, are introduced e.g. through the urethra to the working location, commonly the prostate. Cutting is effected at that point with reciprocating movement of the instrument in the longitudinal direction, which is controlled via its carrier by an operating member disposed beyond the proximal end of the tubular shaft. The instrument is generally a cutting loop to which HF is applied but can also be a knife for special applications. Such resectoscopes may also be used for other applications, for instance in the gynaecological field.

In order to be able to make precise cuts with the instrument, e.g. the cutting loop, in the field of view in front of the optical system, the instrument must be reliably guided by means of its carrier with respect to its radial spacing and its angle of rotation whilst ensuring easy longitudinal movability.

The conventional prior art is shown in FIG. 4 of the aforementioned publication. The carrier is mounted with a sliding tube connected to it on the optical system so as to be longitudinally moveable but at a guaranteed radial spacing, namely on the portion of the optical system which projects distally beyond an optical guide tube connected to the resectoscope and serving to reliably guide and mount it.

The circumferential angular guidance is problematic in this construction. The conventional prior art in this connection is illustrated in FIG. 4 of the aforementioned publication. Connected to the optical guide tube and parallel to it is a carrier guide tube, through which the carrier longitudinally moveably passes and which imparts to the carrier the desired rotational location.

Of disadvantage with this conventional prior art is the additionally necessary carrier guide tube, which is provided parallel on the optical guide tube and is connected to it, for instance by soldering and results in a complex construction of the optical guide tube and which is particularly difficult to clean by reason of its small diameter, which is necessary for reliable guidance.

SUMMARY OF THE INVENTION

The object of the present invention resides in structurally improving the rotational location in a resectoscope of the type referred to above.

In accordance with the invention, provided on the carrier there is a bar, which may be introduced in the sliding direction of the carrier from the distal end into the slot in the optical guide tube and there secures its rotary position about the axis of the optical system whilst ensuring the longitudinal movability of the carrier. Together with the sliding tube, which is in any event present, the result is a highly precise guidance of the carrier and thus of the instrument. This is a very simple construction, in which only one simple bar is necessary on the carrier and, on the endoscope, merely one slot in the optical guide tube, which does not impair its characteristics, may be simply manufactured in the form of a cut out and does not impair the cleaning possibilities of the resectoscope.

With a single cut, which with modern laser cutting technology can be accomplished with suitable contour guidance when cutting the optical guide tube to size, the distal end of the sliding tube can be cut away in a suitable shape such that it not only forms the sliding tube but also, in its proximal region, the bar, which will fit extremely precisely into the slot remaining in the optical guide tube after cutting out the bar. This cut away end portion need only be connected to the carrier in the same manner as the sliding tube is connected in the prior art.

In order to facilitate the introduction of the carrier, the proximal end of the bar can be tapered to a point or of rounded shape and the entry region of the slot can be broadened in the same manner, e.g. of conical shape. Thus even if the insertion is effected "blind", a clean introduction is always achieved, even if the angular position is not exact.

BRIEF DESCRIPTION OF THE DRAWINGS

The invention is schematically illustrated by way of example in the drawings, in which.

DETAILED DESCRIPTION OF THE INVENTION

Figure 1:
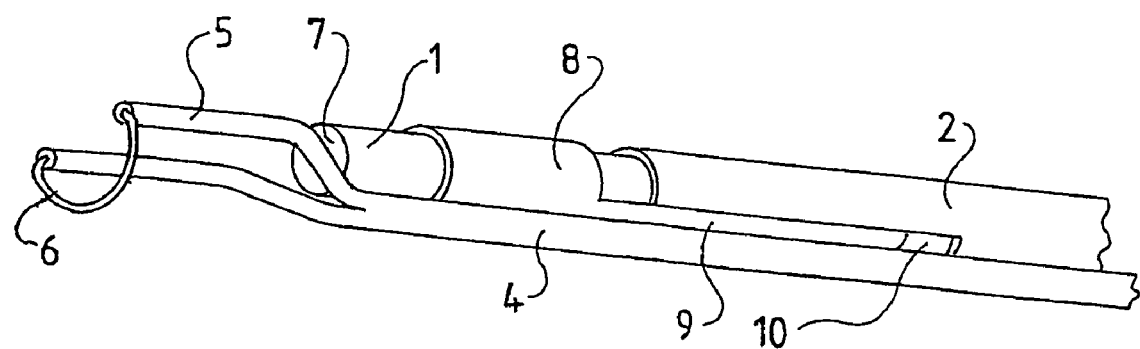
FIG. 1 is a perspective view of a resectoscope in accordance with the invention in the distal end region of the optical system, without the tubular shaft.
Figure 2:
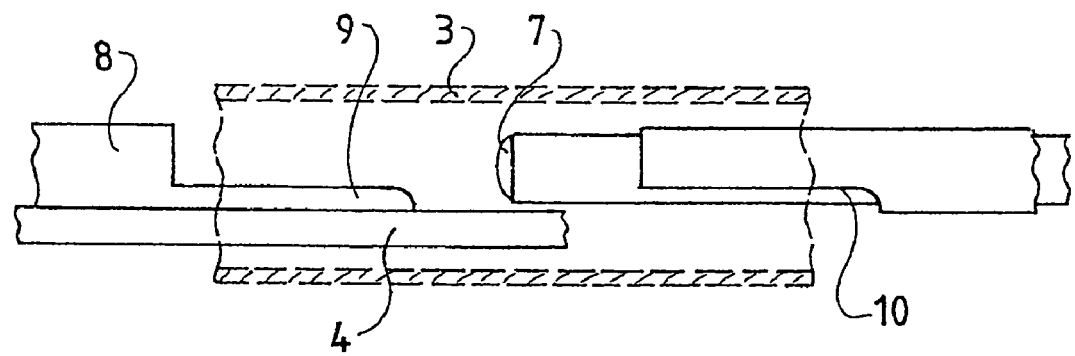
FIG. 2 is a side view of FIG. 1, with the tubular shaft.

The figures show the distal end region of an optical system 1 and an optical guide tube 2 of a resectoscope, the remainder of which is omitted for simplification of the drawing and which otherwise can be constructed e.g. in accordance with FIG. 2 of DE 3603785 A1.

The optical guide tube 2 is connected to a main body, not shown, of the resectoscope, to which the tubular shaft 3, which is shown in chain lines in FIG. 2, is connected, optionally removably.

Extending through the main body is an elongate, rod-shaped carrier 4, which extends within the tubular shaft 3 parallel to the optical system 1 and is actuated in the longitudinal direction by a sliding member, which is provided proximally of the main body and is not illustrated.

The carrier 4 extends within the tubular shaft 3 to the distal end region of the optical system 1 and then branches in the conventional construction to form a fork 5, which carries a cutting loop 6. The latter is electrically connected to an HF connector by an electrical conductor, which passes through the externally insulated carrier 4, on the proximal end of the carrier 4, which is not shown. In another construction, the carrier 4 can carry a non-electric knife at its end.

Work is performed with reciprocating movement in the longitudinal direction with the instrument carried by the carrier 4, the cutting loop 6 in the exemplary embodiment, whilst viewing though the objective 7 provided at the distal end of the optical system 1. In order to ensure reliable working, the cutting loop 6 must be reliably positioned by means of the carrier 4, as regards both its radial spacing from the axis of the optical system 1 and in the circumferential rotational angular direction, with respect to this axis.

For the purpose of radial guidance, connected to the carrier 4 is a sliding tube 8, which is longitudinally moveably guided on the region of the optical system 1 projecting beyond the distal end of the optical guide tube 2.

For the purpose of rotational angular location, a bar 9 is connected to the carrier 4, which engages in a distally open slot 10 in the optical guide tube 2 to be neatly longitudinally guided.

The sliding tube 8 and bar 9 can be constructed in the form of components connected separately to the carrier 4. However, in the illustrated embodiment, they are of one-piece construction in the form of a tubular member appropriately cut to size.

As shown in the figures, the component consisting of the sliding tube 8 and bar 9 is of tubular construction so that it fits without a gap after being inserted in the proximal direction until it hits an end stop on the optical guide tube. It can therefore be manufactured in a very simple manner by cutting the component consisting of the sliding tube 8 and bar 9 out of the optical guide tube with a severing cut. A reliable fit is thus ensured.

As may also be seen in the figures, the proximal end of the bar 9 is rounded. The introduction of the bar into the distal end of the slot 10 is thus facilitated. Alternatively or additionally, the distal end of the slot 10 can be conically broadened towards its end in order to facilitate introduction.

The invention claimed is:

1. A urological resectoscope with a tubular shaft (3), having a fixed optical guide tube (2), within which there is an optical system (1), which projects distally beyond the optical guide tube, an elongate, rod-shaped carrier (4), which carries a cutting instrument (6) at its distal end, being longitudinally moveably mounted in the tubular shaft (3) outside the optical guide tube (2), which carrier is held distally from the optical guide tube (2) with a sliding tube (8) on the optical system (1) at a radial spacing from the axis of the optical system (1) and is secured in the peripheral rotary direction to the optical guide tube (2) with a rotary lock (9,10), wherein the rotary lock has a bar (9) parallel to the carrier (4) and connected to it and a distally open elongate slot (10) in the optical guide tube (2).

2. A resectoscope as claimed in claim 1, wherein the sliding tube (8) is integral with the bar (9) in the form of a cut away distal end piece of the optical guide tube (2).

3. A resectoscope as claimed in claim 1, wherein the proximal end of the bar (9) and/or the distal end of the slot (10) are sloped.

* * * * *